(12) United States Patent
Kawamoto et al.

(10) Patent No.: US 7,041,660 B2
(45) Date of Patent: May 9, 2006

(54) CRYSTALLINE 1-METHYLCARBAPENEM DERIVATIVES

(75) Inventors: Isao Kawamoto, Tokyo (JP); Yasuo Shimoj, Tokyo (JP); Hiroshi Fukuhara, Yokohama (JP)

(73) Assignee: Sankyo Company, Limited, Tokyo (JP)

(*) Notice: Subject to any disclaimer, the term of this patent is extended or adjusted under 35 U.S.C. 154(b) by 290 days.

(21) Appl. No.: 10/625,317

(22) Filed: Jul. 23, 2003

(65) Prior Publication Data

US 2004/0132668 A1    Jul. 8, 2004

Related U.S. Application Data

(63) Continuation-in-part of application No. 10/407,546, filed on Apr. 3, 2003, now abandoned, which is a continuation of application No. 10/034,548, filed on Dec. 28, 2001, now abandoned, which is a continuation of application No. PCT/JP00/04496, filed on Jul. 6, 2000.

(30) Foreign Application Priority Data

Jul. 6, 1999    (JP) ................... 11-191368

(51) Int. Cl.
C07D 477/20    (2006.01)
A61K 31/407    (2006.01)
A61P 31/04     (2006.01)

(52) U.S. Cl. .................. 514/210.13; 540/350
(58) Field of Classification Search ........ 540/350; 514/210.1

See application file for complete search history.

(56) References Cited

U.S. PATENT DOCUMENTS 4,260,543 A * 4/1981 Miller .................... 540/350

(Continued)

FOREIGN PATENT DOCUMENTS

EP    0 256 377 A1 Y    2/1988

(Continued)

*Primary Examiner*—Mark L. Berch
(74) *Attorney, Agent, or Firm*—Frishauf, Holtz, Goodman & Chick, P.C.

(57) ABSTRACT

This invention provides crystalline forms of a 1-methylcarbapenem derivative of formula (I-1), (I-2) or (I-3)

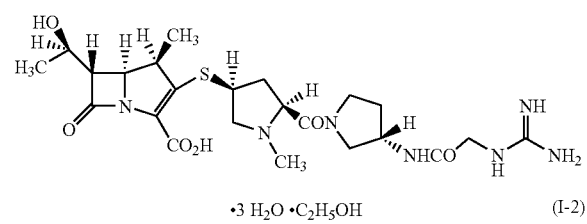

The crystalline forms of the 1-methylcarbapenem derivative exhibit excellent antibiotic activity against various bacterial strains and sufficient stability for practical use.

9 Claims, 4 Drawing Sheets

U.S. PATENT DOCUMENTS

| | | | | |
|---|---|---|---|---|
| 4,713,451 | A * | 12/1987 | Leanza et al. | 540/350 |
| 4,748,238 | A * | 5/1988 | Shih | 540/350 |
| 4,888,344 | A * | 12/1989 | Sunagawa et al. | 540/350 |
| 4,990,613 | A * | 2/1991 | Kumagai et al. | 540/350 |
| 5,424,306 | A * | 6/1995 | Kawamoto et al. | 540/350 |
| 5,550,121 | A | 8/1996 | Nakagawa et al. | |
| 6,090,802 | A | 7/2000 | Kawamoto et al. | |
| 2003/0158174 | A1* | 8/2003 | Kawamoto et al. | 514/210.13 |
| 2004/0198973 | A1* | 10/2004 | Masahiko et al. | 540/350 |

FOREIGN PATENT DOCUMENTS

| | | | |
|---|---|---|---|
| EP | 0 882 728 A1 Y | | 12/1998 |
| HU | 218676 A9 | | 3/1988 |
| HU | 210817 A9 | | 3/1995 |
| JP | 6-336483 | | 12/1994 |
| JP | 07-291973 | | 11/1995 |
| JP | 09-110869 Y | | 4/1997 |
| JP | HEI-11-071277 | | 3/1999 |
| JP | 2001114759 A | * | 4/2001 |
| JP | 2002161034 A | * | 6/2002 |
| JP | 2005-97278 A | * | 4/2005 |

* cited by examiner

CRYSTALLINE 1-METHYLCARBAPENEM DERIVATIVES

This is a Continuation-in-Part application of Ser. No. 10/407,546 filed Apr. 3, 2003 now abandoned which is a continuation application of Ser. No. 10/034,548 filed Dec. 28, 2001, now abandoned which is a continuation application of PCT/JP00/04496 filed Jul. 6, 2000 (not published in English).

BACKGROUND OF THE INVENTION

1. Field of the Invention

This invention is directed to crystalline forms of 1-methylcarbapenem derivatives or of pharmaceutically acceptable salts thereof which exhibit excellent antibiotic activity against various bacterial strains and are stable enough to keep for a long time.

This invention is directed compositions for the prevention or treatment of bacterial infections containing a crystalline form of the present invention as an active ingredient.

This invention is directed to uses of a crystalline form of the present invention in order to prepare a medicament for the prevention or treatment of bacterial infections.

This invention is directed to methods for the preventing or treating bacterial infections which comprise administering to a warm-blooded animal in need of such prevention or treatment an effective amount of a crystalline form of the present invention.

Further this invention is directed to processes for the preparation of crystalline forms of the present invention.

2. Description of Related Art

The 1-methylcarbapenem derivative of formula (I) is disclosed in Japanese Patent Application Publication Hei-10-204086 and Hei-11-071277 and in U.S. Pat. No. 6,090,802 (corresponds to Hei-10-204086). This compound (I) exhibits excellent antibiotic activity not only against Gram-positive bacterial strains but also against Gram-negative bacterial strains and can be expected to become a useful antibiotic agent. However, the compound (I) prepared according to the Example of Japanese Patent Application Publication Hei-11-071277 (which is Example 72 of U.S. Pat. No. 6,090,802) was obtained by lyophilization as a non-crystalline powder. This powder is unstable and is a material difficult to keep for a long time. There are many problems in practical use of the powder as a medicament, especially as an antibiotic agent. The inventors made many efforts in order to solve these problems and have found that certain crystalline forms of compound (I) are extremely stable compared to the non-crystalline powder of compound (I) and are useful medicaments, especially, practically useful antibiotic agents. The stable crystalline forms of this invention include a crystalline form of compound (I) containing 3 hydrate and 1 ethanol (I-1), a crystalline form of compound (I) containing ½ ethanol (I-2), a crystalline form of compound (I) and a crystalline form of compound (I) containing ¼ ethanol and ½ water (I-3).

BRIEF DESCRIPTION OF THE INVENTION

This invention is directed to 1. a 1-methylcarbapenem derivative of formula (I) or a pharmaceutically acceptable salt thereof in crystalline form,

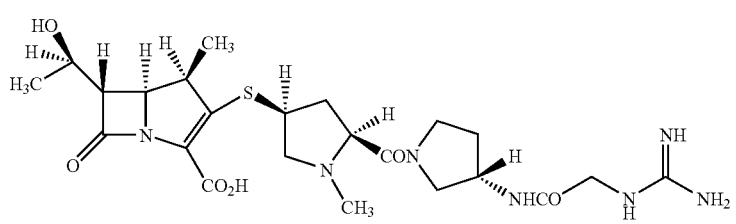

(I)

2. a 1-methylcarbapenem derivative of formula (I-1) in crystalline form,

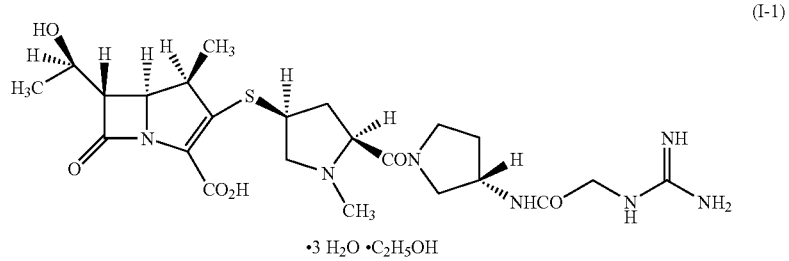

(I-1)

·3 $H_2O$ ·$C_2H_5OH$ 3. a 1-methylcarbapenem derivative of formula (I-2) in crystalline form,

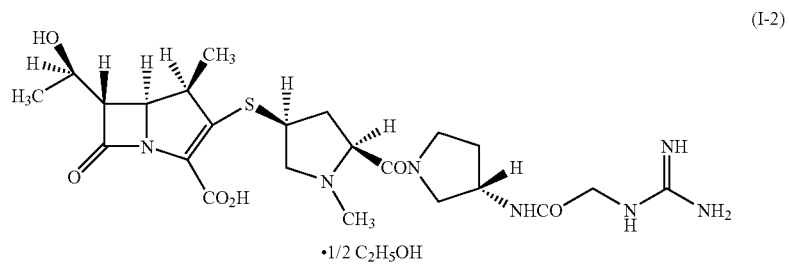

(I-2)

·1/2 C$_2$H$_5$OH 4. a 1-methylcarbapenem derivative of formula (I) in crystalline form,

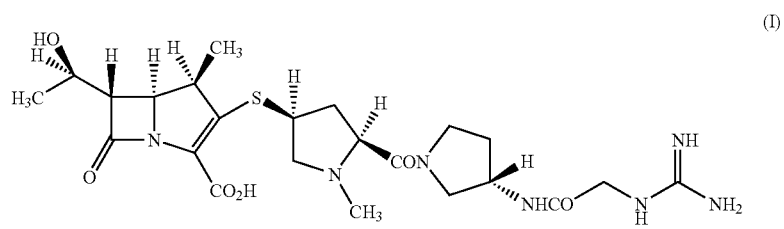

(I)

5. a 1-methylcarbapenem derivative of formula (I-3) in crystalline form,

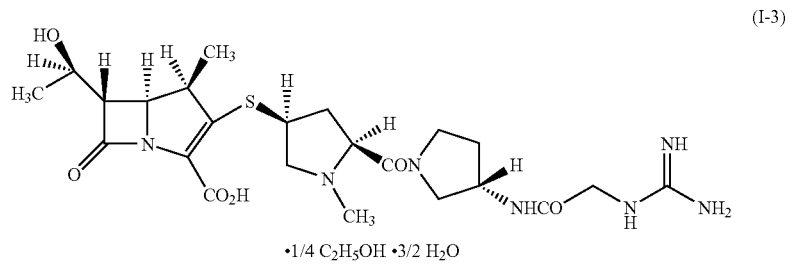

(I-3)

·1/4 C$_2$H$_5$OH ·3/2 H$_2$O 6. pharmaceutical compositions for the prevention or treatment of bacterial infections containing a crystalline form of a 1-methylcarbapenem derivative according to any one of 1 to 5 as an active ingredient,
7. uses of a crystalline form of a 1-methylcarbapenem derivative according to any one of 1 to 5 in order to prepare a medicament for the prevention or treatment of bacterial infections, and
8. methods for preventing or treating bacterial infections which comprise administering to a warm-blooded animal in need of such prevention or treatment an effective amount of a crystalline form of a 1-methylcarbapenem derivative according to any one of 1 to 5.

DETAILED DESCRIPTION

Carbapenem derivatives of formula (I) are disclosed in U.S. Pat. No. 6,090,802 and Japanese Patent Application Publications Hei-10-204086 and Hei-11-071277, and exhibit potent activity against Gram-positive and Gram-negative bacterial strains.

Carbapenem derivatives of formula (I) can exist as pharmaceutically acceptable salts. The term "a pharmaceutically acceptable salt" as used herein and in the claims is intended to include salts which are usually able to be used as medicaments.

The compound of formula (I) has basic groups such as a tertiary amino group and a guanidino group and can be converted to a pharmaceutically acceptable acid addition salt when treated with an appropriate acid employing conventional techniques. Such acid addition salts include inorganic acid salts such as hydrochlorides, hydrobromides, sulfates and phosphates; organic acid salts such as carbonates, acetates, benzoates, oxalates, maleates, fumarates, tartrates and citrates; and sulfonates such as methanesulfonates, benzenesulfonates and p-toluenesulfonates.

The compound of formula (I) has an acidic group such as a carboxyl group and can be converted to a pharmaceutically acceptable base addition salt when treated with an appropriate base employing conventional techniques. Such base addition salts include alkali metal salts such as sodium salts, potassium salts and lithium salts; alkaline earth metal salts such as calcium salts and magnesium salts; metal salts such as aluminum salts, iron salts, zinc salts, copper salts, nickel salts, and cobalt salts; and quaternary ammonium salts such as ammonium salts.

When allowed to stand in the air, certain forms of the compound (I) and pharmaceutically acceptable salts thereof absorb or adsorb water and can form hydrates. In certain cases forms of the compound (I) and pharmaceutically acceptable salts thereof absorb certain solvents and can form solvates. The compound (I) of this invention and pharmaceutically acceptable salts thereof include such hydrates and solvates. Such salts, hydrates and solvates are preferably sodium salts, hydrochlorides, sulfates, carbonates, hydrates or solvates of ethanol; most preferably carbonates, hydrates or solvates of ethanol.

The compound of formula (I-1) represents the 3 hydrate and 1 ethanol solvate of the 1-methylcarbapenem derivative of formula (I). The compound of formula (I-2) represent the ½ ethanol solvate of the 1-methylcarbapenem derivative of formula (I). The compound of formula (I-3) represents the ³⁄₂ hydrate and ¼ ethanol solvate of the 1-methylcarbapenem derivative of formula (I).

Crystalline Form:

The crystalline forms of the present invention are solids which have regular arrangements of atoms (group of atoms) in three-dimensional structure and repeat the arrangements. The crystals are different from an amorphous solid that has no such regular arrangement of atoms in a three-dimensional structure.

In general, certain compounds produce a plurality of crystalline forms (polymorphic crystals) according to crystallization conditions, crystals of which are different in their three-dimensional arrangement of atoms and in physicochemical properties. This invention may include each of such crystalline forms and mixtures no less than two thereof.

The crystalline form of the 1-methylcarbapenem derivative of formula (I-1) shows main peaks at interplanar spacings d=6.65, 5.68, 4.86, 4.57 and 4.03 Å in the X-ray powder diffraction pattern obtained with a Cu $K_\alpha$ irradiation of $\lambda$=1.54 Å. The main peaks have intensities not less than 74, which is the relative intensity when the intensity of the peak at 4.57 Å is evaluated as 100.

The crystalline form of the 1-methylcarbapenem derivative of formula (I-2) shows main peaks at interplanar spacings d=10.57, 7.12, 5.34, 5.23, 4.91 and 4.26 Å in the X-ray powder diffraction pattern obtained with a Cu $K_\alpha$ irradiation of $\lambda$=1.54 Å. The main peaks have intensities not less than 56, which is the relative intensity when the intensity of the peak at 4.91 Å is evaluated as 100.

The crystalline form of the 1-methylcarbapenem derivative of formula (I) shows main peaks at interplanar spacings d=8.07, 5.08, 4.89, 4.44, 4.39 and 4.19 Å in the X-ray powder diffraction pattern obtained with a Cu $K_\alpha$ irradiation of $\lambda$=1.54 Å. The main peaks have intensities not less than 48, which is the relative intensity when the intensity of the peak at 5.08 Å is evaluated as 100.

The crystalline form of the 1-methylcarbapenem derivative of formula (I-3) shows main peaks at interplanar spacings d=7.02, 4.90, 4.64, 4.59 and 4.03 Å in the X-ray powder diffraction pattern obtained with a Cu $K_\alpha$ irradiation of $\lambda$=1.54 Å. The main peaks have intensities not less than 65, which is the relative intensity when the intensity of the peak at 7.02 Å is evaluated as 100.

Preparation:

The compound of formula (I) can be prepared by the same technique as described, or by a similar procedure to that described in U.S. Pat. No. 6,090,802, Japanese Patent Application Publication Hei-10-204086 and Hei-11-071277.

The crystalline forms of this invention were obtained, for example, 1) by dissolution of compound (1) or a pharmaceutically acceptable salt thereof in an appropriate solvent which can readily dissolve it,
2) by, if necessary, concentration of the solution, addition to the solution of an appropriate solvent which can slightly dissolve compound (I) or a pharmaceutically acceptable salt thereof or cooling the solution in order to obtain a supersaturated solution and hence to crystallization, and
3) by isolation of the crystals and then drying of the crystals.

Precipitation of the crystals begins spontaneously in the vessel, or precipitation can also begin or be accelerated by addition of crystalline seeds or by mechanical stimulations such as ultrasonic wave irradiation and scratching on the surface of the vessel.

Pharmaceutically acceptable salts of compound (I) are preferably hydrochlorides, sulfates and carbonates; most preferably carbonates. The pharmaceutically acceptable salts can be prepared by addition of necessary amount of a desired acid or base to a solution of compound (I).

When solutions of the compound (I) or pharmaceutically acceptable salts thereof are treated, the solutions of these compounds are usually treated between 0 and 60° C. in order to avoid decomposition of these compounds.

The preferred temperature of crystallization of these compounds is between 0 and 10° C.

Methods of concentration of solutions of the compound (I) or pharmaceutically acceptable salts thereof are an evaporation method using a rotary evaporator under reduced or normal pressure upon heating and a concentration method using a reverse osmotic membrane. The reverse osmotic membrane used in concentration of an aqueous solution can be selected from polyacrylonitrile membranes, polyvinyl alcohol membranes, polyamide membranes and cellulose acetate membranes.

Examples of solvents which can readily dissolve compound (I) or pharmaceutically acceptable salts thereof are water, dimethyl sulfoxide, dimethylformamide and methanol, preferably water.

Examples of solvents which can slightly dissolve compound (I) or pharmaceutically acceptable salts thereof are $C_2$–$C_4$ alcohols such as ethanol, propanol and butanol; ketones such as acetone and methyl ethyl ketone; ethers such as diethyl ether and tetrahydrofuran; and esters such as methyl acetate and ethyl acetate; preferably ethanol and acetone; most preferably ethanol.

The starting compound (I) which is isolated as a lyophilized powder can be used. A crude reaction solution containing compound (I) can also be used because it is possible to purify by crystallization.

Supersaturation can be accomplished by concentration of an aqueous solution of compound (I) at between 30 and 60° to a saturated aqueous solution, followed by gradually cooling to between 0 and 10° C. or accomplished by gradual addition of an appropriate solvent which can slightly dissolve compound (I) or pharmaceutically acceptable salts thereof, such as ethanol or acetone, to the saturated aqueous solution, if necessary, followed by cooling.

Crystalline forms of this invention preferably precipitate when aqueous solutions of compound (I) or pharmaceutically acceptable salts are concentrated, if necessary, followed by the addition of a solvent which can slightly dissolve these compounds, followed by cooling. More preferably crystals of this invention precipitate when aqueous solutions of compound (I) or pharmaceutically acceptable salts thereof are concentrated, if necessary, followed by the addition of ethanol or acetone and then cooling.

Most preferably, the preferred crystalline form of compound (I-1) precipitates when an aqueous solution of compound (I) is concentrated, followed by saturation with carbon dioxide, addition of ethanol and cooling; the preferred crystalline form of compound (I-2) precipitates when an aqueous solution of compound (I) is concentrated, followed by the addition of ethanol and by cooling (preferably by irradiation with ultrasonic waves); the preferred crystalline form of compound (I) precipitates when an aqueous solution of compound (I) is concentrated, followed by cooling; the preferred crystalline form of compound (I-3) precipitates when an aqueous solution of compound (I) is concentrated, followed by addition of ethanol and by cooling.

The precipitated crystals are isolated, for example, by filtration, centrifugation or decantation. If necessary, the isolated crystals can be washed with an appropriate solvent. Preferably the crystals are washed at first with the solvent which is used in crystallization, and then washed with a solvent such as ethanol, acetone, and ether.

The isolated crystals are dried at between 10 and 50° C., preferably at between 20 and 30° C. until the weight of the crystals become constant. If necessary, they may be dried in the presence of drying agents such as silica gel and calcium chloride under reduced pressure.

Utility:

The crystalline forms of compound (I-1), (I-2), (I) and (I-3) are easy to use practically as a medicament and are extremely stable compared to the lyophilized powder of compound (I) which is disclosed in Japanese Patent Application Publication Hei-11-071277.

The crystalline forms of this invention exhibit a wide spectrum of antibiotic activity and potent antibacterial activities against Gram-positive and Gram-negative strains and anerobic bacteria, as well as bacteria producing cephalosporinase. When the antibacterial activities of the crystals of this invention were determined by the agar-plate dilution method, they exhibited potent antibacterial activities against various bacteria, for example, Gram-positive strains such as *Staphylococcus aureus*, methicillin-resistant *Staphylococcus aureus, Streptococcus pneumoniae, Enterococcus* and the like; Gram-negative strains such as *Escherichia coli, Bacillus dysenteriae, Klebsiella pneumoniae, Proteus vulgaris, Serratia, Enterobacteriaceae, Pseudomonas aeruginosa* and the like; and anerobic bacteria such as *bacteroides fragilis*. The crystalline forms of this invention exhibited potent antibacterial activity against Helicobacter pylori which is often detected in the patients with chronic gastritis and peptic ulcers.

When appropriate solutions of the crystalline forms of this invention were administered to mice, they exhibited long half-value periods of blood concentration and good urinary recovery compared to those of similar compounds known to those skilled in the art.

When the crystalline forms of this invention were subcutaneously administered to mice infected systemically with *Staphylococcus aureus, Streptococcus pneumoniae, Escherichia coli* or *Psuedomonas aeruginosa*, they exhibited excellent treatment effect. The crystalline forms of this invention, therefore, are useful medicaments (especially antibacterial agents).

When the crystalline forms of this invention are used as a medicament (especially as an antibacterial agent) they can be administered alone or as a mixture of said crystalline forms of this invention and a pharmaceutically acceptable excipient(s) and diluent(s); they can be administered in various dosage forms such as tablets, capsules, granules, powders, or syrups for oral administration, such as injections for parenteral administration or such as ointments for topical application.

Such dosage forms are prepared by methods known to those skilled in the art using additives such as excipients, binders, disintegrants, lubricants, stabilizers, corrigents, suspending agents, diluents, solvents for formulation, assisting agents for dissolution, and topical anaesthetic agents.

Examples of excipients include sugar derivatives such as lactose, sucrose, glucose, mannitol and sorbitol; starch derivatives such as corn starch, potato starch, α starch, dextrin and carboxymethylstarch; cellulose derivatives such as crystalline cellulose, low-substituted hydroxypropylcellulose, hydroxypropylmethylcellulose; carboxymethylcellulose and internally-cross-linked sodium carboxymethylcellulose; arabic gum; dextran; pululan; silicate derivatives such as light silicic acid anhydride, synthetic aluminum silicate and magnesium aluminate metasilicate; phosphate derivatives such as calcium phosphate; carbonate derivatives such as calcium carbonate, and sulfate derivatives such as calcium sulfate.

Examples of binders include excipients as described above; gelatin; polyvinylpyrrolidone; and macrogol.

Examples of disintegrants include excipients as described above, and chemically modified starch and cellulose derivatives such as sodium cross-carmelose, sodium carboxymethylstarch and cross-linked polyvinylpyrrolidone.

Examples of lubricants include talc; stearic acid; metal stearate derivatives such as calcium stearate and magnesium stearate; colloidal silica; bee gum; waxes such as bee's wax and spermaceti; boric acid; glycol; carboxylic acid derivatives such as fumaric acid and adipic acid; sodium carboxylate derivatives such as sodium benzoate; sulfate derivatives such as sodium sulfate; leucine; lauryl sulfate derivatives such as sodium lauryl sulfate and magnesium lauryl sulfate; silicic acid derivatives such as silicic acid anhydride and silicic acid hydrate; and starch derivatives as described for the excipients.

Examples of stabilizers include para-oxybenzoic acid esters such as methylparaben and propylparaben; alcohols such as chlorobutanol, benzyl alcohol, and phenethyl alcohol; benzalkonium chloride; phenol derivatives such as phenol and cresol; thimerosal; acetic anhydride, and sorbic acid.

Examples of corrigents include sweetening, souring and flavoring agents all of which are usually used.

Examples of solvents for formulation include water, ethanol, and glycerin.

Examples of assisting agents for dissolution include nonionic surfactants, and anionic surfactants.

Examples of topical anaesthetic agents include lidocaine hydrochloride, and mepivacaine hydrochloride.

Dosage forms for oral administration include, for example, solid dosage forms such as tablets, coated tablets, capsules, troches, powders, fine granules, granules, and dry syrups and liquid dosage forms such as syrups. Dosage forms for parenteral administration include, for example, injections, dripping infusions and suppositories. Dosage forms for topical application include, for example, ointments, tinctures, creams, and gels.

Preferable dosage forms of the crystalline 1-methylcarbapenem derivatives of this invention are injections and dripping infusions. Suitable dosage levels for the crystalline forms depend on the age, body weight, and symptoms of the patient and are usually from 10 mg (preferably 50 mg) to 6000 mg (preferably 4000 mg) for an adult human per day, which dosage can be administered as a single dose or divided into several doses throughout the day.

EXAMPLES

The following examples, reference examples, test examples and formulation examples further illustrate this invention.

All NMR spectra in examples and reference examples were determined in deuterated water using tetramethylsilane or in another solvent using sodium 3-(trimethylsilyl)propionate as internal standards, respectively.

Throughout the chemical structures the following abbreviations are used with the following meaning:
PNB: 4-nitrobenzyl
PNZ: 4-nitrobenzyloxycarbonyl

Example 1

(1R,5S,6S)-2-[(2S,4S)-2-[(3S)-3-(2-Guanidinoacetylamino)pyrrolidin-1-ylcarbonyl]-1-methylpyrrolidin-4-ylthio]-6-[(1R)-1-hydroxyethyl]-1-methyl-1-carbapen-2-em-3-carboxylic acid.3 hydrate.ethanol

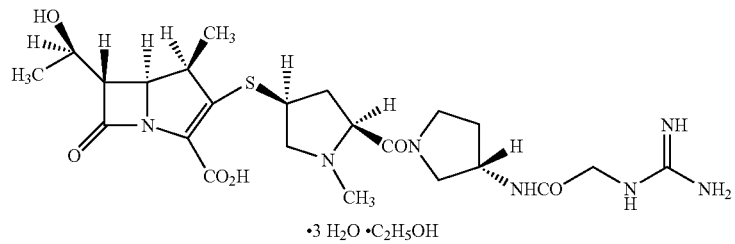

·3 H$_2$O ·C$_2$H$_5$OH

To a solution of 4-nitrobenzyl (1R,5S,6S)-2-[(2S,4S)-2-[(3S)-3-[2-[2,3-bis(4-nitrobenzyloxycarbonyl)guanidino]acetylamino]pyrrolidin-1-ylcarbonyl]-1-methylpyrrolidin-4-ylthio]-6-[(1R)-1-hydroxyethyl]-1-methyl-1-carbapen-2-em-3-carboxylate (9.4 g) in a mixture of tetrahydrofuran (235 ml) and water (140 ml) was added 7.5% palladium on carbon (9.4 g, which contains water (53.1%)) and the resulting mixture was stirred under a hydrogen atmosphere at 35° C. for 2 hours. At the end of this time the catalyst was removed by filtration and the filtrate was washed with ether. The ether and tetrahydrofuran were evaporated in vacuo and the resulting residue was chromatographed on a reverse phase column (Cosmosil 75C18PREP (trade mark) manufactured by Nacalai tesque Inc.) using a mixture of acetonitrile and water as the eluant. The fractions containing the desired product were combined and concentrated to approximately 50 ml in vacuo. Ethanol (100 ml) and dry ice were added to the concentrate and the resulting solution was allowed to stand in an ice bath. The resulting precipitate was filtered and washed successively with a mixture of ethanol and water (2:1), ethanol and ether to afford the title compound as colorless crystals (3.15 g).

Melting point: 228–233° C. (dec)

Infrared spectrum (KBr) ν max cm$^{-1}$: 3331, 2968, 2875, 2791, 1755, 1669,1637, 1453, 1386, 1339, 1312, 1283, 1254.

NMR spectrum (400 MHz, D$_2$O) δ ppm: 1.13–1.24 (4.5H, m), 1.30 (3H, d, J=6.4 Hz), 1.57–1.72 (1H, m), 1.93–2.10 (1H, m), 2.15–2.35 (1H, m), 2.27, 2.29 (3H, s×2), 2.68–2.88 (2H, m), 3.09 (1H, d, J=10.6 Hz), 3.29–3.73 (7H, m), 3.75–3.93 (2H, m), 4.01 (2H, s), 4.12–4.30 (2H, m), 4.38–4.50 (1H, m).

A X-ray powder diffraction pattern of the crystalline product shown in FIG. 1 was obtained with a Cu K$_\alpha$ irradiation of λ=1.54 Å. The vertical axis of the x-ray powder diffraction pattern indicates the diffraction intensity in units of counts/second (CPS). The horizontal axis indicates the diffraction angle as the value 2θ. The interplanar spacing d can be calculated using the equation $2d \sin \theta = n\lambda$ in which n is 1.

Example 2

(1R,5S,6S)-2-[(2S,4S)-2-[(3S)-3-(2-Guanidinoacetylamino)pyrrolidin-1-ylcarbonyl]-1-methylpyrrolidin-4-ylthio]-6-[(1R)-1-hydroxyethyl]-1-methyl-1-carbapen-2-em-3-carboxylic acid.½ ethanol

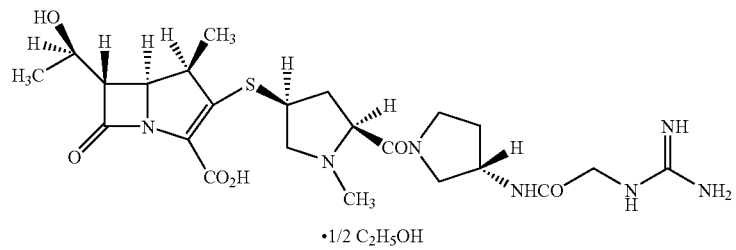

·1/2 C$_2$H$_5$OH

To a solution of 4-nitrobenzyl (1R,5S,6S)-2-[(2S,4S)-2-[(3S)-3-[2-[2,3-bis(4-nitrobenzyloxycarbonyl)guanidino]-acetylamino]pyrrolidin-1-ylcarbonyl]-1-methyl-pyrrolidin-4-ylthio]-6-[(1R)-1-hydroxyethyl]-1-methyl-1-carbapen-2-em-3-carboxylate (10.00 g) in a mixture of tetrahydrofuran (250 ml) and water (150 ml) was added 7.5% palladium on carbon (10.00 g, which contains water (53.1%)) and the resulting mixture was stirred under a hydrogen atmosphere at 35° C. for 2 hours. At the end of this time the catalyst was removed by filtration, the filtrate was washed with ether and was filtered through a membrane filter. The resulting filtrate was concentrated to approximately 50 ml in vacuo. To the concentrate was added ethanol (100 ml) and the resulting mixture was irradiated with ultrasonic waves in order to precipitate crystals, and then allowed to stand in an ice bath. The precipitated crystals were filtered and washed successively with a mixture of ethanol and water (2:1), ethanol and ether and then dried to afford the title compound as colorless crystals (3.30 g).

Melting point: 235–250° C. (dec)

Infrared spectrum (KBr) ν max cm$^{-1}$: 3405, 3344, 3273, 3207, 2969, 2883, 2795, 1760, 1673, 1644, 1591, 1553, 1452, 1415, 1381, 1370, 1341, 1311, 1283, 1255.

NMR spectrum (400 MHz, $D_2O$) δ ppm: 1.15–1.25 (4.5H, m), 1.30 (3H, d, J=6.4 Hz), 1.57–1.72 (1H, m), 1.93–2.13 (1H, m), 2.15–2.35 (1H, m), 2.27, 2.29 (3H, s×2), 2.68–2.88 (2H, m), 3.08 (1H, d, J=10.7 Hz), 3.29–3.73 (7H, m), 3.75–3.93 (2H, m), 4.01 (2H, s), 4.16–4.31 (2H, m), 4.37–4.49 (1H, m).

Elemental analysis: calculated for $C_{23}H_{35}N_7O_6S \cdot \frac{1}{2}C_2H_6O$ Cal.: C 51.41%; H 6.83%; N 17.49%; S 5.72%; Found: C 51.13%; H 6.96%; N 17.17%; S 5.72%

A X-ray powder diffraction pattern of the crystalline product shown in FIG. 2 was obtained with a Cu $K_\alpha$ irradiation of λ=1.54 Å. The vertical axis of the x-ray powder diffraction pattern indicates the diffraction intensity in units of counts/second (CPS). The horizontal axis indicates the diffraction angle as the value 2θ. The interplanar spacing d can be calculated using the equation 2d sin θ=nλ in which n is 1.

Example 3

(1R,5S,6S)-2-[(2S,4S)-2-[(3S)-3-(2-Guanidinoacetylamino)pyrrolidin-1-ylcarbonyl]-1-methylpyrrolidin-4-ylthio]-6-[(1R)-1-hydroxyethyl]-1-methyl-1-carbapen-2-em-3-carboxylic acid.½ ethanol

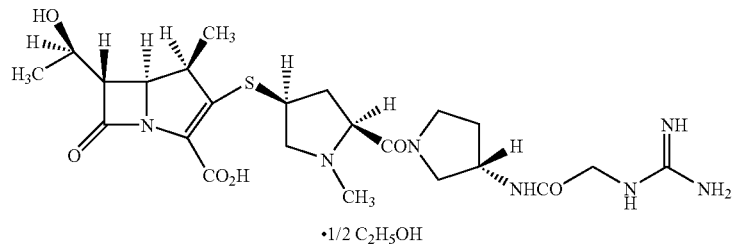

·1/2 $C_2H_5OH$

To a solution of 4-nitrobenzyl (1R,5S,6S)-6-[(1R)-1-hydroxyethyl]-1-methyl-2-[(2S,4S)-1-methyl-2-[(3S)-3-[2-[3-(4-nitrobenzyloxycarbonyl)guanidino]-acetylamino]pyrrolidin-1-ylcarbonyl]pyrrolidin-4-ylthio]-1-carbapen-2-em-3-carboxylate (112 mg) in a mixture of tetrahydrofuran (2.2 ml) and water (2.2 ml) was added 7.5% palladium on carbon (112 mg, which contains water (53.1%)) and the resulting mixture was stirred under a hydrogen atmosphere at 35° C. for 2 hours. At the end of this time the catalyst was removed by filtration and the filtrate was washed with ether and was filtered through a membrane filter. The filtrate was concentrated to approximately 1 ml in vacuo. To the resulting concentrate was added ethanol (2 ml) and the mixture was irradiated with ultrasonic waves in order to precipitate crystals, and then allowed to stand in an ice bath. The precipitated crystals were filtered and washed successively with a mixture of ethanol and water (2:1), ethanol and ether and then dried to afford the title compound (45 mg) as colorless powder. The melting point, infrared spectrum, NMR spectrum, elemental analysis and x-ray powder diffraction pattern of this product were identical with those of the compound obtained in Example 2.

Example 4

(1R,5S,6S)-2-[(2S,4S)-2-[(3S)-3-(2-Guanidinoacetylamino)pyrrolidin-1-ylcarbonyl]-1-methylpyrrolidin-4-ylthio]-6-[(1R)-1-hydroxyethyl]-1-methyl-1-carbapen-2-em-3-carboxylic acid

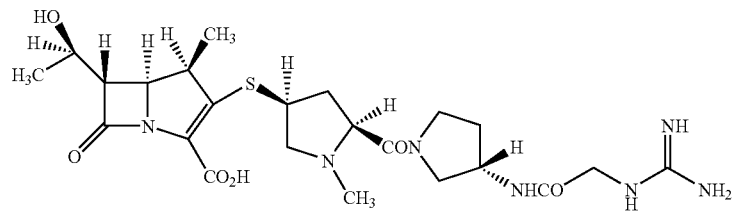

(1) (1R,5S,6S)-2-[(2S,4S)-2-[(3S)-3-(2-Guanidinoacetylamino]pyrrolidin-1-ylcarbonyl]-1-methylpyrrolidin-4-ylthio]-6-[(1R)-1-hydroxyethyl]-1-methyl-1-carbapen-2-em-3-carboxylic acid.½ ethanol (680 mg) was dissolved in water (35 ml). The mixture was filtered through a membrane filter. The filtrate was concentrated to approximately 3 ml in vacuo. The resulting concentrate was allowed to stand at 0° C. overnight. The precipitated crystals were filtered and washed with a small amount of water and then dried to afford the title compound as colorless crystals (294 mg).

Melting point: 235–250 (dec)

Infrared spectrum (KBr) ν max cm$^{-1}$: 3327, 3177, 3068, 2970, 2904, 2880, 2820, 1751, 1681, 1654, 1629, 1594, 1572, 1536, 1481, 1440, 1423, 1382, 1336, 1314, 1286, 1264.

NMR spectrum (400 MHz, D$_2$O) δ ppm: 1.20 (3H, dd, J=7.2, 2.2 Hz), 1.30 (3H, d, J=6.4 Hz), 1.57–1.72 (1H, m), 1.93–2.13 (1H, m), 2.15–2.35 (1H, m), 2.27, 2.29 (3H, s×2), 2.68–2.88 (2H, m), 3.09 (1H, d, J=10.5 Hz), 3.29–3.73 (6H, m), 3.75–3.93 (2H, m), 4.01 (2H, s), 4.16·4.31 (2H, m), 4.37–4.49 (1H, m).

Elemental analysis: calculated for C$_{23}$H$_{35}$N$_7$O$_6$S Cal.: C 51.38%; H 6.56%; N 18.24%; S 5.96%; Found: C 51.14%; H 6.85%; N 18.26%; S 6.04%

A X-ray powder diffraction pattern of the crystalline product shown in FIG. 3 was obtained with a Cu K$_\alpha$ irradiation of λ=1.54 Å. The vertical axis of the x-ray powder diffraction pattern indicates the diffraction intensity in units of counts/second (CPS). The horizontal axis indicates the diffraction angle as the value 2θ. The interplanar spacing d can be calculated using the equation 2d sin θ=nλ in which n is 1.

(2) A similar procedure to that described above was carried out on the same scale as Example 3. To the resulting concentrate (about 1 ml) was added a small amount of the colorless crystals prepared as described in Example 4 (1) and the resulting mixture was allowed to stand at 0° C. overnight. The precipitated crystals were collected by filtration and washed with a small amount of water to afford the title compound (20 mg).

Example 5

(1R,5S,6S)-2-[(2S,4S)-2-[(3S)-3-(2-Guanidinoacetylamino)pyrrolidin-1-ylcarbonyl]-1-methylpyrrolidin-4-ylthio]-6-[(1R)-1-hydroxyethyl]-1-methyl-1-carbapen-2-em-3-carboxylate.¼ ethanol.³⁄₂ hydrate

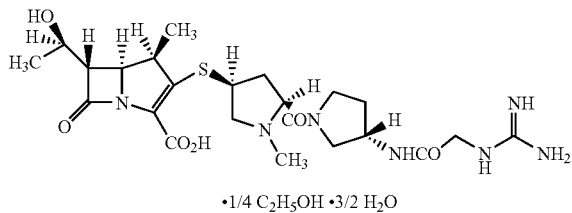

·¼ C$_2$H$_5$OH ·3/2 H$_2$O

To a solution of 4-nitrobenzyl (1R,5S,6S)-6-[(1R)-1-hydroxyethyl]-1-methyl-2-[(2S,4S)-1-methyl-2-[(3S)-3-[2-[3-(4-nitrobenzyloxycarbonyl)guanidino]-acetylamino]pyrrolidin-1-ylcarbonyl]pyrrolidin-4-ylthio]-1-carbapen-2-em-3-carboxylate (220 g) in a mixture of tetrahydrofuran (2200 ml) and water (2200 ml) was added 7.5% palladium on carbon (220 g, which contains water (53.1%)) and the resulting mixture was stirred under a hydrogen atmosphere at 30° C. for 2 hours. At the end of this time the catalyst was removed by filtration and the filtrate was washed with ethyl acetate and was filtered through a membrane filter. The filtrate was concentrated to approximately 600 ml. To the concentrate was added ethanol (1800 ml) and the resulting mixture was stirred until crystals were precipitated, and then this allowed to stand in an ice bath. The precipitated crystals were filtered and washed successively with a mixture of ethanol and water (3:1) and ethanol and then dried to afford the title compound (40 g) as colorless crystals.

Melting point: 226–245° C. (dec)

Infrared spectrum (KBr) ν max cm$^{-1}$: 3409, 3345. 3275, 3185, 2967, 2884, 1761, 1674, 1644, 1586, 1551, 1452, 1415, 1380, 1369, 1340, 1282, 1254.

NMR spectrum (400 MHz, D$_2$O) δ ppm: 1.17–1.21 (4.7H, in), 1.30 (3H, d, J=6.4 Hz), 1.57–1.70 (1H, m), 1.95–2.08 (1H, m), 2.18–2.31 (1H, m), 2.27, 2.29, (3H, s×2), 2.70–2.87 (2H, m), 3.08 (1H, d, J=10.8 Hz), 3.31–3.72 (7H, m), 3.76–3.92 (2H, m), 4.00 (2H, S), 4.18·4.28 (2H, m), 4.39·4.48 (1H, m).

Elemental analysis: calculated for C$_{23}$H$_{35}$N$_7$O$_6$S.¼C$_2$H$_6$O.³⁄₂H$_2$O Cal.: C 48.99%; H 6.91%; N 17.02%; S 5.56%; Found: C 48.35%; H 6.47%; N 17.23%; S 5.67%

A X-ray powder diffraction pattern of the crystalline product shown in FIG. 4 was obtained with a Cu K$_\alpha$ irradiation of λ=1.54 Å. The vertical axis of the x-ray powder diffraction pattern indicates the diffraction intensity in units of counts/second (CPS). The horizontal axis indicates the diffraction angle as the value 2θ. The interplanar spacing d can be calculated using the equation 2d sin θ=nλ in which n is 1.

Reference Example 1

4-Nitrobenzyl (1R,5S,6S)-2-[(2S,4S)-2-[(3S)-3-[2-[2,3-bis(4-nitrobenzyloxycarbonyl)guanidino]-acetylamino]pyrrolidin-1-ylcarbonyl]-1-methylpyrrolidin-4-ylthio]-6-[(1R)-1-hydroxyethyl]-1-methyl-1-carbapen-2-em-3-carboxylate

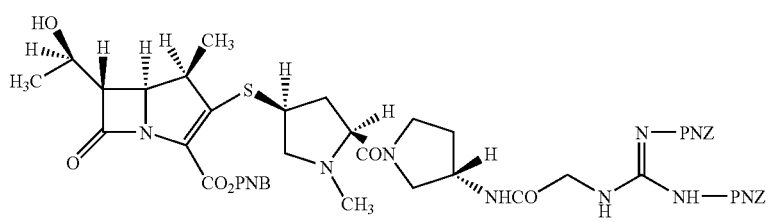

Hydrazine acetate (652 mg) was added to a solution of (2S,4S)-4-acetylthio-2-[(3S)-3-[2-[2,3-bis(4-nitrobenzyloxycarbonyl)guanidino]acetylamino]pyrrolidin-1-ylcarbonyl]-1-methylpyrrolidine (4.3 g) in N,N-dimethylformamide (86 ml) and stirred at room temperature for 4 hours. To the resulting mixture was added 4-nitrobenzyl (1R,5R,6S)-6-[(1R)-1-hydroxyethyl]-1-methyl-2-diphenylphosphoryloxy-1-carbapen-2-em-3-carboxylate (3.53 g) and N,N-diisopropylethylamine (1.34 ml) and allowed to react at −30° C. for 3 days. At the end of this time, to the reaction mixture was added 1% aqueous sodium hydrogencarbonate solution and the resulting precipitate was filtered, washed with water, and dissolved in a mixture of tetrahydrofuran and ethyl acetate (3:7). The resulting solution was washed successively with saturated aqueous sodium hydrogencarbonate solution, water and saturated aqueous sodium chloride solution, dried over anhydrous magnesium sulfate and concentrated in vacuo. The resulting residue was chromatographed on a silica gel column using 10% methanol/ethyl acetate and 20% methanol/ethyl acetate as the eluant to afford the crude desired product. The product was dissolved in tetrahydrofuran and reprecipitated with a mixture of ethyl acetate and ether (1:1) to give the desired compound (4.02 g) as a pale yellow powder.

Infrared spectrum (KBr) ν max $cm^{-1}$: 3336, 1772, 1741, 1688, 1643, 1610, 1522, 1447, 1378, 1347.

NMR spectrum (270, $CDCl_3$) δ ppm: 1.17–1.40 (6H, m), 1.64–2.40 (4H, m), 2.33 (3H, s), 2.47–2.80 (2H, m), 3.00–3.38 (3H, m), 3.46–3.83 (5H, m), 3.93–4.60 (5H, m), 5.12–5.54 (6H, m), 7.21 (1H, d, J=6.5 Hz), 7.46–7.70 (6H, m), 8.10–8.28 (6H, m), 8.80–9.10 (1H, br), 11.60 (1H, br).

Reference Example 2

4-Nitrobenzyl (1R,5S,6S)-6-[(1R)-1-hydroxyethyl]-1-methyl-2-[(2S,4S)-2-[(3S)-3-[2-[3-(4-nitrobenzyloxycarbonyl)guanidino]acetylamino]pyrrolidin-1-ylcarbonyl]-1-methylpyrrolidin-4-ylthio]-1-carbapen-2-em-3-carboxylate vacuo. The resulting residue was chromatographed on a reverse phase column (Cosmosil 75C18PREP (trade mark) manufactured by Nacalai tesque Inc.) using a mixture of acetonitrile and water as the eluant. The fractions containing the desired product were combined and concentrated in vacuo. The residue was powdered in a mixture of ethyl acetate and isopropyl ether. Powdery (2S,4S)-4-mercapto-1-methyl-2-[(3S)-3[2-[3-(4-nitrobenzyloxycarbonyl)guanidino]acetylamino]pyrrolidin-1-yl-carbonyl]pyrrolidine (806 mg) was obtained by filtration.

Infrared spectrum (KBr) ν max $cm^{-1}$: 3391, 3307, 3112, 3078, 2949, 2877, 2786, 1732, 1639, 1548, 1522, 1448, 1380,.1347, 1291, 1211, 1154, 1109.

NMR spectrum (400 MHz, $CDCl_3$) δ ppm: 1.64–2.15 (3H, m), 2.20–2.86 (5H, m), 2.93–3.93 (9H, m), 4.16–4.35 (1H, m), 5.12 (2H, s), 6.70–6.90 (1H, br), 7.00–7.85 (1H, br), 7.59 (2H, d, J=8.5 Hz), 8.23 (2H, d, J=8.5Hz), 8.18–8.40 (1H, br).

(2) N,N-Diisopropylethylamine (0.17 ml) and 4-nitrobenzyl (1R,5R,6S)-6-[(1R)-1-hydroxyethyl]-1-methyl-2-diphenylphosphoryloxy-1-carbapen-2-em-3-carboxylate (585 mg) were added to a solution of the compound (500 mg) obtained in Reference example 2 (1) in N,N-dimethylformamide (5 ml) in an ice bath and allowed to react at 0° C. overnight. At the end of this time, ethyl acetate and tetrahydrofuran were added to the reaction mixture, the resulting mixture was washed with 10% aqueous sodium chloride solution and concentrated in vacuo. The resulting residue was chromatographed on a reverse phase column (Cosmosil 75C18PREP (trade mark) manufactured by Nacalai tesque Inc.) using a mixture of acetonitrile and water as the eluant. The fractions containing the desired product were combined and concentrated in vacuo. The resulting reside was powdered in isopropyl ether and filtered to afford the desired compound (524 mg) as a pale yellow powder.

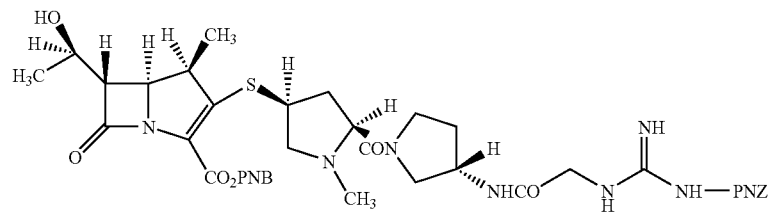

(1) A solution of 28% sodium methylate in methanol (0.5 ml) was added to a solution of (2S,4S)-4-acetylthio-1-methyl-2-[(3S)-3-[2-[3-(4-nitrobenzyloxycarbonyl)guanidino]acetylamino]pyrrolidin-1-ylcarbonyl]pyrrolidine (1.5 g) in methanol (30 ml) and stirred at room temperature for I hour. At the end of this time, to the resulting mixture was added 1N hydrochloric acid (2.73 ml) and concentrated in Infrared spectrum (KBr) ν max $cm^{-1}$: 3384, 3113, 3080, 2970, 2875, 2789, 1770, 1643, 1609, 1522, 1450, 1379, 1346, 1322, 1287, 1209, 1181, 1136, 1109.

NMR spectrum (400 MHz, $CDCl_3$) δ ppm: 1.08–2.22 (6H, m), 1.75–2.26 (6H, m), 2.44–2.76 (2H, m), 2.89–3.00 (1H, m), 3.03–3.15 (1H, m), 3.18–3.65 (6H, m), 3.68–3.90 (3H, m), 3.53–4.06 (1H, m), 4.13–4.35 (2H, m), 5.05–5.15 (2H, m), 5.30, 5.45 (each 1H, d, J=14.1), 7.58 (2H, dd, J=8.8, 2.7 Hz), 7.74 (2H, d, J=8.7 Hz), 8.18–8.33 (4H, m).

Reference Example 3

4-Nitrobenzyl (1R,5S,6S)-6-[(1R)-1-hydroxyethyl]-1-methyl-2-[(2S,4S)-2-[(3S)-3-[2-[3-(4-nitrobenzyloxycarbonyl)guanidino]acetylamino]pyrrolidin-1-ylcarbonyl]-1-methylpyrrolidin-4-ylthio]-1-carbapen-2-em-3-carboxylate

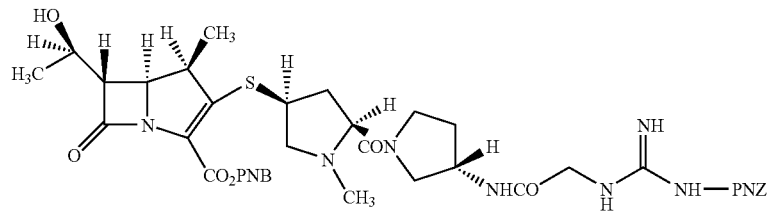

To a solution of (2S,4S)-4-acetylthio-1-methyl-2-[(3S)-3-[2-[3-(4-nitrobenzyloxycarbonyl)guanidino]acetylamino]pyrrolidin-1-ylcarbonyl]pyrrolidine (500 mg) in ethanol (5 ml) was added 4N hydrogen chloride/ethyl acetate (2.7 ml) and stirred at 50° C. for 3 hours. At the end of this time, ether was added to the reaction mixture. The resulting precipitate was separated by decantation and dried in vacuo. To a solution of the precipitate in N,N-dimethylformamide (10 ml) were added N,N-diisopropylethylamine (0.63 ml) and 4-nitrobenzyl (1R,5R,6S)-6-[(1R)-1-hydroxyethyl]-1-methyl-2-diphenylphosphoryloxy-1-carbapen-2-em-3-carboxylate (541 mg) in an ice bath and allowed to react overnight. At the end of this time, to the reaction mixture was added 1% aqueous sodium hydrogencarbonate solution. The resulting precipitate was filtered, washed with water and dried. The crude powder was chromatographed on a silica gel column using 30% methanol/ethyl acetate and 50% methanol/ethyl acetate as the eluant to give the desired compound (446 mg). The Infrared and NMR spectra of this compound were identical with those of the compound obtained in Reference example 2 (2).

Reference Example 4

4-Nitrobenzyl (1R,5S,6S)-6-[(1R)-1-hydroxyethyl]-1-methyl-2-[(2S,4S)-2-[(3S)-3-[2-[3-(4-nitrobenzyloxycarbonyl)guanidino]acetylamino]pyrrolidin-1-ylcarbonyl]-1-methylpyrrolidin-4-ylthio]-1-carbapen-2-em-3-carboxylate

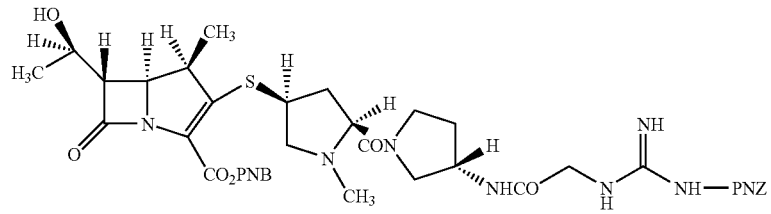

To a solution of (2S,4S)4-acetylthio-1-methyl-2-[(3S)-3-[2-[3-(4-nitrobenzyloxycarbonyl)guanidino]acetylamino]pyrrolidin-1-ylcarbonyl]pyrrolidine (1.00 g) in methanol (20 ml) was added sodium methylate (98.3 mg) at 0° C. and stirred for 1 hour. At the end of this time, to the reaction mixture was added 4N hydrogen chloride/ethyl acetate (0.46 ml) and concentrated in vacuo. In an ice bath to a solution of the resulting residue in N,N-dimethylformamide (10 ml) were added a solution of N,N-diisopropylethylamine (0.32 ml) and 4-nitrobenzyl (1R,5R,6S)-6-[(1R)-1-hydroxyethyl]-1-methyl-2-diphenylphosphoryloxy-1-carbapen-2-em-3-carboxylate (1.08 g) in N,N-dimethylformamide and allowed to stand at 0° C. overnight. At the end of this time, to the reaction mixture was added 1% aqueous sodium hydrogencarbonate solution. The resulting precipitate was filtered, washed with water and dried. The crude powder was chromatograhed on a silica gel column using methanol/ethyl acetate=⅓ and methanol/ethyl acetate=½ as the eluant to give the desired compound (975 mg). The Infrared and NMR spectra of this compound were identical with those of the compound obtained in Reference example 2-(2).

Test Example 1

Stability Test

The crystalline compounds obtained in Example 1, 2, 4 and 5 were kept for about 2 months in a desiccator at 40° C. and 75% relative humidity and in a desiccator at 60° C. in which silica gel was placed, respectively. The non-crystalline powdered compound (lyophilized product) obtained according to the procedure described in U.S. Pat. No. 6,090,802 Example 72 and in Japanese Patent Application Publication No. Hei-11–071277, which is a reference sample, was kept under the same conditions described above. The remaining amount of the crystalline compounds and the non-crystalline powdered compound were determined after 7, 20, 21, 28, and 56 days by high pressure liquid chromatography on a L-Column ODS (4.6 mm Φ×150 mm, (trade mark) manufactured by Kagakuhinn kennsa kyoukai) eluting with 20 mM $KH_2PO_4$ (pH 7.0): $CH_3CN$=96:4 at 1.0 ml/minute at 60° C. using an ultraviolet wave length of 300 nm. The remaining percentages of these-compounds were calculated from the remaining amount of them and show in Tables 1–4.

TABLE 1

Stability in desiccator at 40° C. and 75% relative humidity

| Compound | Remaining percentage of compound | |
|---|---|---|
| | After 20 days | After 56 days |
| Crystals obtained in Example 1 | 98.5 | 92.9 |
| Crystals obtained in Example 2 | 95.8 | 87.3 |
| Crystals obtained in Example 4 | 99.4 | 94.3 |
| Non-crystalline powder (lyophilized product) | 30.2 | 0.3 |

TABLE 2

Stability in desiccator at 60° C. in which silica gel was placed

| Compound | Remaining percentage of compound | |
|---|---|---|
| | After 21 days | After 56 days |
| Crystals obtained in Example 1 | 98.5 | 96.4 |
| Crystals obtained in Example 2 | 100.1 | 96.8 |
| Crystals obtained in Example 4 | 100.4 | 100.9 |
| Non-crystalline powder (lyophilized product) | 74.1 | 56.5 |

TABLE 3

Stability in desiccator at 40° C. and 75% relative humidity

| Compound | Remaining percentage of compound | | |
|---|---|---|---|
| | After 7 days | After 28 days | After 56 days |
| Crystals obtained in Example 5 | 98.9 | 94.6 | 83.2 |

TABLE 4

Stability in desiccator at 60° C. in which silica gel was placed

| Compound | Remaining percentage of compound | | |
|---|---|---|---|
| | After 7 days | After 28 days | After 56 days |
| Crystals obtained in Example 5 | 98.3 | 97.0 | 97.6 |

From the Tables 1 and 3, it is clear that the non-crystalline powder of compound (1) (lyophilized product) was very unstable at 40° C. and 75% relative humidity, that is, after 20 days the percentage of remaining amount of the compound is 30.2% and after 56 days it is only 0.3%, and that the percentages of remaining amount of the crystalline compounds of this invention are more than 83, respectively under the same conditions.

From the Tables 2 and 4, it is clear that the non-crystalline powder of compound (I) (lyophilized product) was also unstable at 60° C. under dry conditions, that is, after 21 days the percentage of remaining amount of the compound is 74.1% and after 56 days that is 56.5%, and that the percentages of remaining amount of the crystalline compounds of this invention are more than 96, respectively under the same conditions.

These results show that the crystalline compounds of this invention are extremely stable compared to the non-crystalline powder (lyophilized product) belonging to the previous invention.

Test Example 2

Antibiotic Activity Test

The MIC (µg/ml), the lowest concentration of antibiotic which inhibits growth of the test bacterial strain, was determined by the agar-plate dilution method. The crystalline compounds obtained in Example 1, 2, 4 and 5 of this invention were evaluated against various bacterial strains by determining the MIC of each compound with respect to each strain. Table 5 illustrates the result of such experiments.

TABLE 5

Antibiotic activity (MIC, µg/ml)

| | Crystalline compounds obtained in | | | |
|---|---|---|---|---|
| Bacterial strain | Example 1 | 2 | 4 | 5 |
| *Staphylococcus aureus* 209P | 0.01 | 0.01 | 0.01 | 0.01 |
| *S. aureus* 535 (MRSA) | 1.5 | 1.5 | 1.5 | 1.5 |
| *Escherichia coli* NIHJ | 0.01 | 0.01 | 0.01 | 0.01 |
| *E. coli* 609 | 0.02 | 0.01 | 0.02 | 0.01 |
| *Klebisella pneumoniae* 806 | 0.01 | 0.01 | 0.01 | 0.01 |
| *K. pneumoniae* 846 | 0.01 | 0.01 | 0.01 | 0.01 |
| *Enterobacter cloacae* 963 | 0.05 | 0.05 | 0.05 | 0.05 |
| *Serratia marcescens* 1184 | 0.01 | 0.01 | 0.01 | 0.01 |
| *Pseudomonas aeruginosa* 1001 | 0.2 | 0.2 | 0.2 | 0.39 |

Formulation Example 1

Injections

The crystalline compound obtained in Example 1 (250 mg) is used to fill a vial and shielded with a stopper under sterile conditions. Pharmaceutical additives known to those skilled in the art such as a local anaesthetic agent, for example, lidocaine hydrochloride can be added to the vial, if necessary. The sterile solid compositions can be dissolved in an injectable medium such as water for injection immediately before use.

The diffraction pattern was obtained with a Cu $K_\alpha$ irradiation of $\lambda=1.54$ Å to the crystals. The vertical axis of the x-ray powder diffraction pattern indicates the diffraction intensity in units of counts/second (CPS). The horizontal axis indicates diffraction angle as the value $2\theta$.

Figure 1:
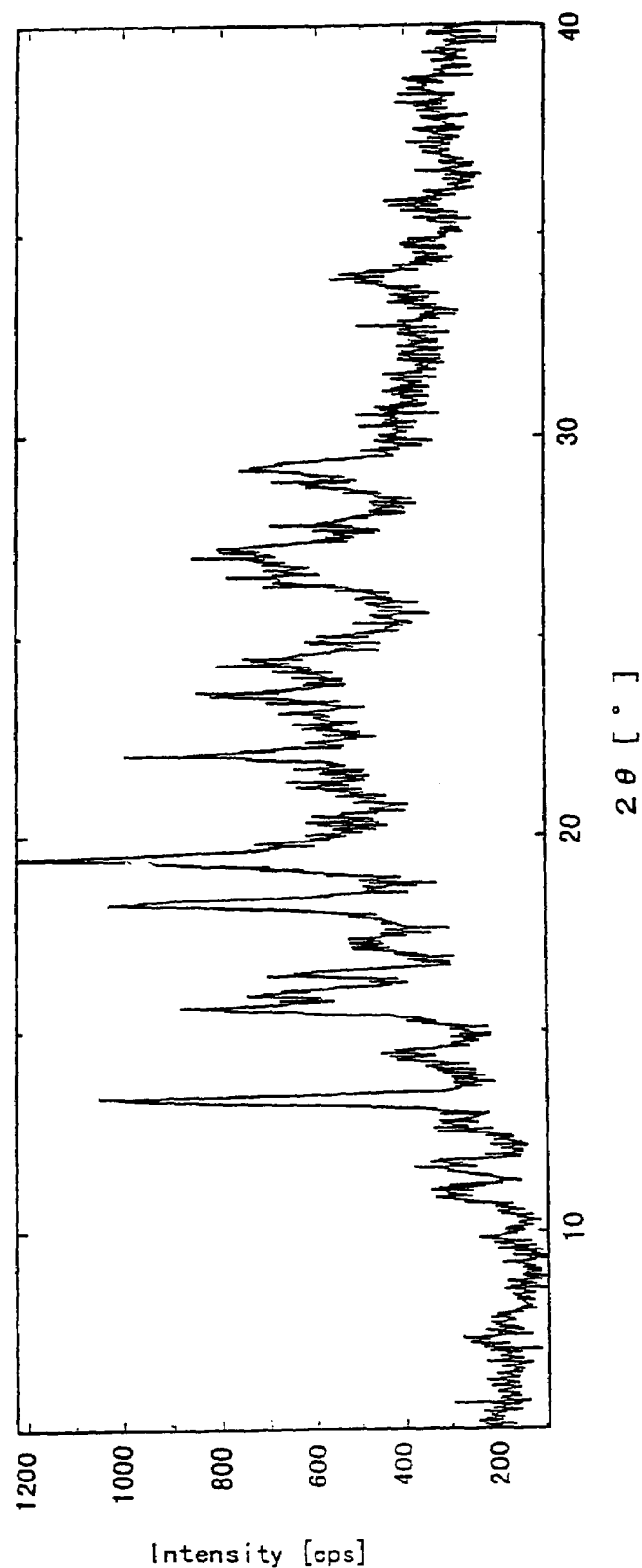
FIG. 1 shows the powder diffraction pattern of crystalline (1R,5S,6S)-2-[(2S,4S)-2-[(3S)-3-(2-guanidinoacetylamino) pyrrolidin-1-ylcarbonyl]-1-methylpyrrolidin-4-ylthio]-6-[(1R)-1-hydroxyethyl]-1-methyl-1-carbapen-2-em-3-carboxylic acid.3 hydrate.1 ethanol (I-1).
Figure 2:
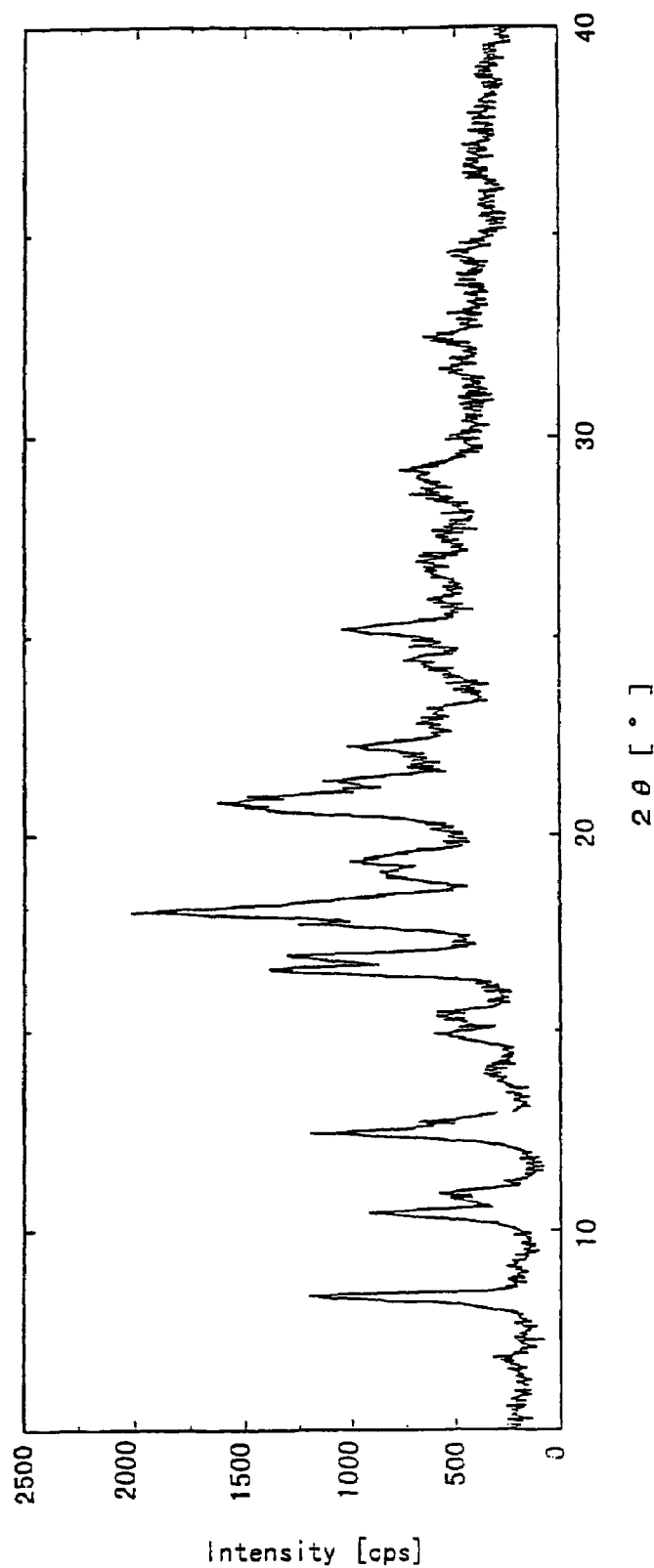

FIG. 2 shows the x-ray powder diffraction pattern of crystalline (1R,5S,6S)-2-[(2S,4S)-2-[(3S)-3-(2-guanidinoacetylamino)pyrrolidin-1-ylcarbonyl]-1-methyl-pyrrolidin-4-ylthio]-6-[(1R)-1-hydroxyethyl]-1-methyl-1-carbapen-2-em-3-carboxylic acid.½ ethanol (I-2).

The diffraction pattern was obtained with a Cu $K_\alpha$ irradiation of $\lambda=1.54$ Å to the crystals. The vertical axis of the x-ray powder diffraction pattern indicates the diffraction intensity in units of counts/second (CPS). The horizontal axis indicates diffraction angle as the value $2\theta$.

Figure 3:
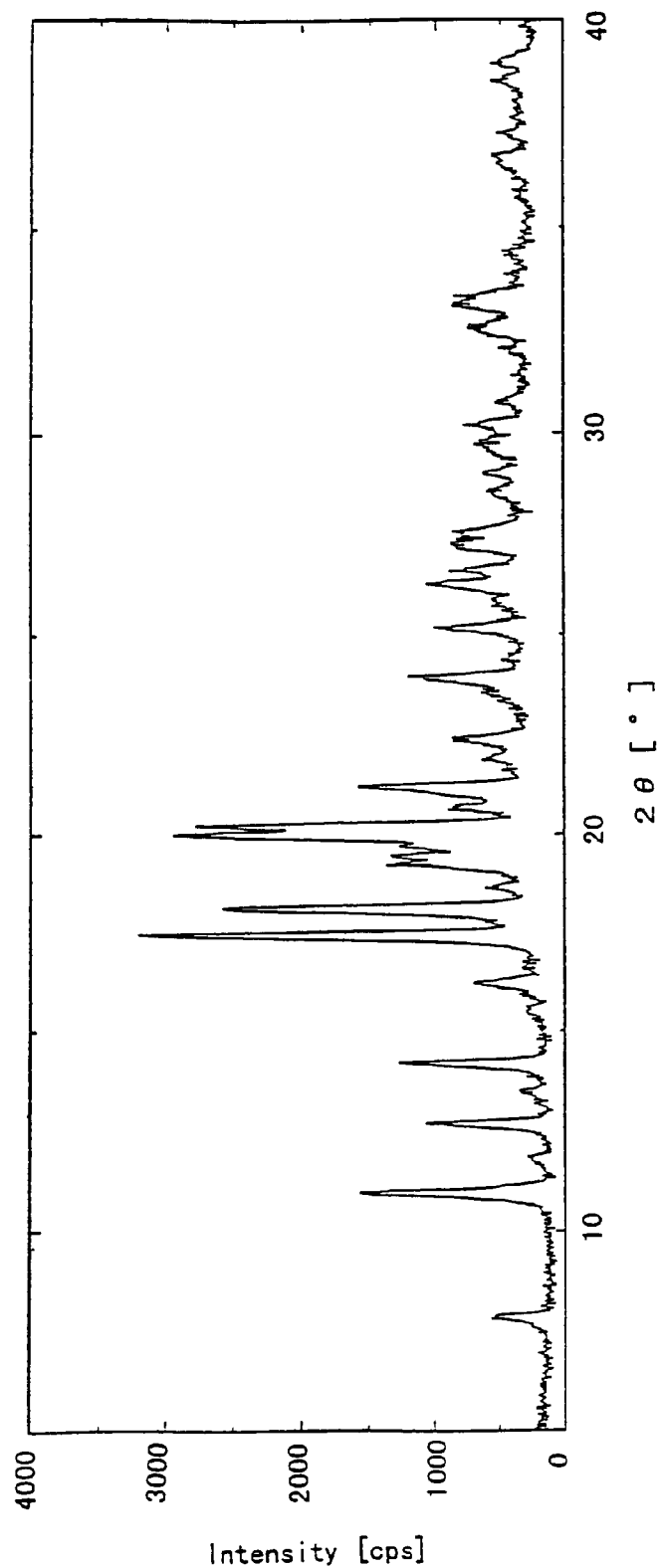

FIG. 3 shows the x-ray powder diffraction pattern of (1R,5S,6S)-2-[(2S,4S)-2-[(3S)-3-(2-guanidinoacetylamino)pyrrolidin-1-ylcarbonyl]-1-methylpyrrolidin-4-ylthio]-6-[(1R)-1-hydroxyethyl]-1-methyl-1-carbapen-2-em-3-carboxylic acid (I).

The diffraction pattern was obtained with a Cu $K_\alpha$ irradiation of $\lambda=1.54$ Å to the compound (I). The vertical axis of the x-ray powder diffraction pattern indicates the diffraction intensity in units of counts/second (CPS). The horizontal axis indicates diffraction angle as the value $2\theta$.

Figure 4:
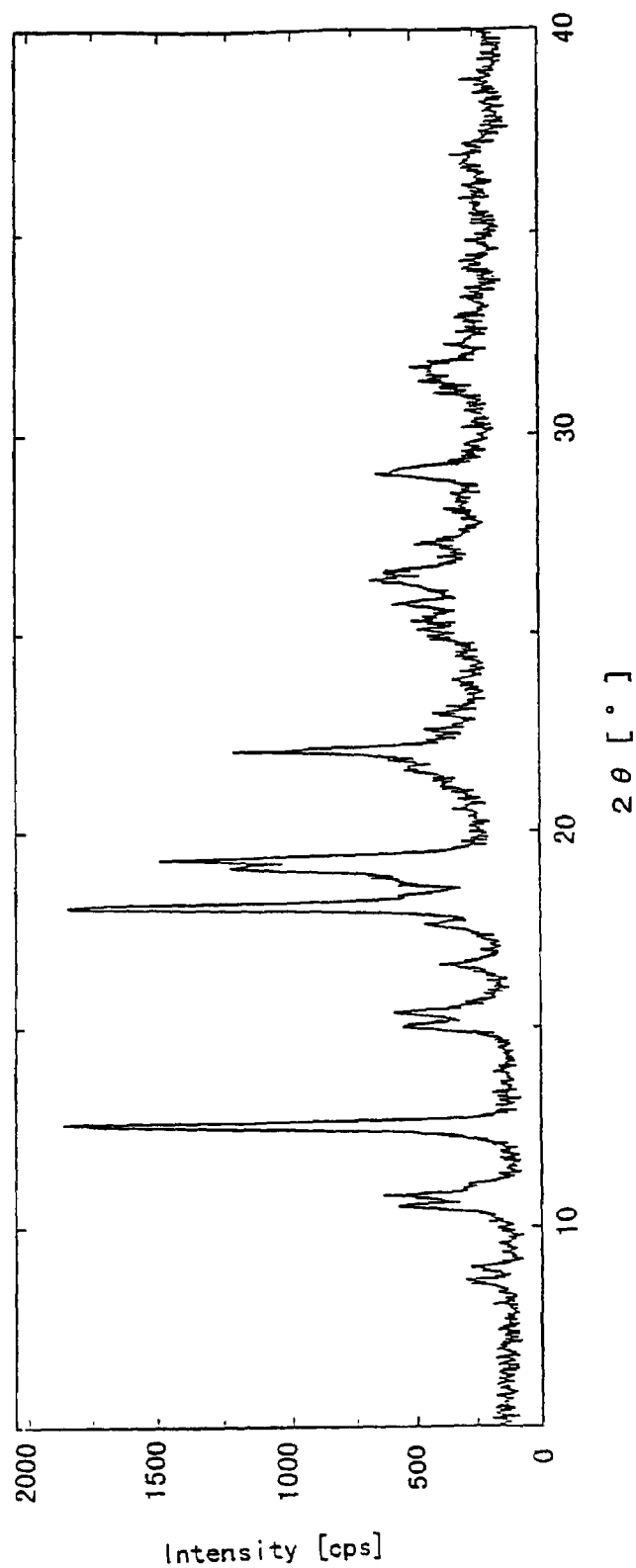

FIG. 4 shows the x-ray powder diffraction pattern of crystalline (1R,5S,6S)-2-[(2S,4S)-2-[(3S)-3-(2-guanidinoacetylamino)pyrrolidin-1-ylcarbonyl]-1-methyl-pyrrolidin-4-ylthio]-6-[(1R)-1-hydroxyethyl]-1-methyl-1-carbapen-2-em-3-carboxylic acid.¼ ethanol.³⁄₂ hydrate (I-3).

The diffraction pattern was obtained with a Cu $K_\alpha$ irradiation of $\lambda=1.54$ Å to the crystals. The vertical axis of the x-ray powder diffraction pattern indicates the diffraction intensity in units of counts/second (CPS). The horizontal axis indicates diffraction angle as the value $2\theta$.

What is claimed is:

1. A 1-methylcarbapenem derivative of formula (I-1) in crystalline form, wherein the crystalline form shows main peaks at interplanar spacings d=6.65, 5.68, 4.86, 4.57 and 4.03 Å in the X-ray powder diffraction pattern obtained with a Cu $K_\alpha$ irradiation of $\lambda=1.54$ Å, the main peaks having relative intensities not less than 74, relative to the intensity of the peak at 4.57 Å which is evaluated as 100

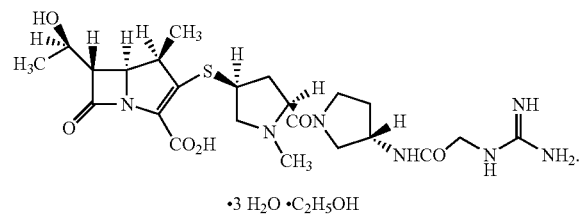

(I-1)

·3 H₂O ·C₂H₅OH

2. A 1-methylcarbapenem derivative of formula (I-2) in crystalline form:

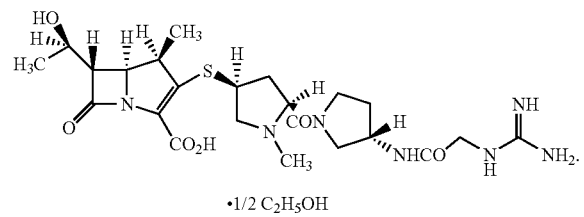

(I-2)

·1/2 C₂H₅OH

3. A 1-methylcarbapenem derivative of formula (I-3) in crystalline form:

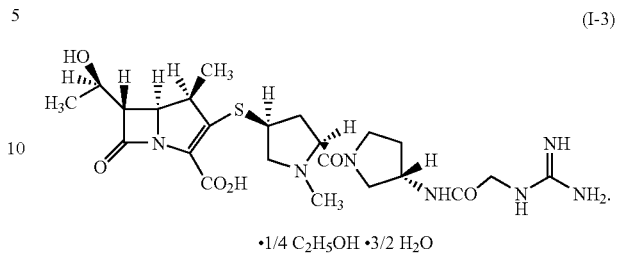

(I-3)

·1/4 C₂H₅OH ·3/2 H₂O

4. A solid pharmaceutical composition for the prevention or treatment of bacterial infections comprising a therapeutically effective amount of a 1-methylcarbapenem derivative of formula (I-1) in crystalline form as claimed in claim 1 as an active ingredient together with a diluent or carrier therefor.

5. A solid pharmaceutical composition for the prevention or treatment of bacterial infections comprising a therapeutically effective amount of a 1-methylcarbapenem derivative of formula (I-2) in crystalline form as claimed in claim 2 as an active ingredient together with a diluent or carrier therefor.

6. A solid pharmaceutical composition for the prevention or treatment of bacterial infections comprising a therapeutically effective amount of a 1-methylcarbapenem derivative of formula (I-3) in crystalline form as claimed in claim 3 as an active ingredient together with a diluent or carrier therefor.

7. A method for preventing or treating bacterial infections which comprises administering to a warm-blooded animal in need of such prevention or treatment a pharmacologically effective amount of a 1-methylcarbapenem derivative of formula (I-1) in crystalline form as claimed in claim 1.

8. A method for preventing or treating bacterial infections which comprises administering to a warm-blooded animal in need of such prevention or treatment a pharmacologically effective amount of a 1-methylcarbapenem derivative of formula (I-2) in crystalline form as claimed in claim 2.

9. A method for preventing or treating bacterial infections which comprises administering to a warm-blooded animal in need of such prevention or treatment a pharmacologically effective amount of a 1-methylcarbapenem derivative of formula (I-3) in crystalline form as claimed in claim 3.

* * * * *